(12) United States Patent  
Olcina Portilla

(10) Patent No.: US 9,023,103 B2  
(45) Date of Patent: May 5, 2015

(54) ACCOMMODATIVE INTRAOCULAR LENS

(76) Inventor: Luis Olcina Portilla, Valencia (ES)

(*) Notice: Subject to any disclaimer, the term of this patent is extended or adjusted under 35 U.S.C. 154(b) by 7 days.

(21) Appl. No.: 13/577,200

(22) PCT Filed: Feb. 14, 2011

(86) PCT No.: PCT/EP2011/052125  
§ 371 (c)(1),  
(2), (4) Date: Aug. 3, 2012

(87) PCT Pub. No.: WO2011/101310  
PCT Pub. Date: Aug. 25, 2011

(65) Prior Publication Data  
US 2012/0310345 A1    Dec. 6, 2012

(30) Foreign Application Priority Data  
Feb. 19, 2010  (ES) .................... 201000246

(51) Int. Cl.  
*A61F 2/16*  (2006.01)

(52) U.S. Cl.  
CPC ............ *A61F 2/1613* (2013.01); *A61F 2/1629* (2013.01); *A61F 2/1635* (2013.01); *A61F 2/1648* (2013.01)

(58) Field of Classification Search  
USPC ......................... 623/4.1, 6.38–6.55  
See application file for complete search history.

(56) References Cited

U.S. PATENT DOCUMENTS 6,013,101 A * 1/2000 Israel ................ 623/6.43

| | | |
|---|---|---|
| 2001/0001836 A1 | 5/2001 | Cumming |
| 2004/0162612 A1 | 8/2004 | Portney et al. |
| 2004/0169816 A1 | 9/2004 | Esch |

FOREIGN PATENT DOCUMENTS

| | | | | |
|---|---|---|---|---|
| FR | 2728458 | * | 6/1996 | ............. A61F 2/16 |
| FR | 2728459 | * | 6/1996 | ............. A61F 2/16 |
| FR | 2770394 | * | 5/1999 | ............. A61F 2/16 |
| WO | WO2009021327 | | 2/2009 | |

OTHER PUBLICATIONS

International Search Report issued in connection with International Application No. PCT/EP2011/052125, completed Apr. 19, 2011, mailed Apr. 28, 2011, 3 pages.

* cited by examiner

*Primary Examiner* — Thomas J Sweet  
*Assistant Examiner* — Tiffany Shipmon  
(74) *Attorney, Agent, or Firm* — Vedder Price PC

(57) ABSTRACT

Accommodative intraocular lens comprising an optic part (1), which in turn comprises at least one incurving notch (3) and a peripheral edge of the optic (2); a haptic part (8), which in turn comprises at least one central branch (9), one lateral branch (10) and one angular branch of the haptic (11); an incomplete incurving ring (6) that in turn comprises at least one angled branch of the ring (17); an incurving tab (5); and means for sliding and/or stopping and/or amplifying the moving parts. The new accommodative intraocular lens accommodates in near vision by a posteroanterior displacement of the optic, changes in its curvature and changes in its thickness. The design of the incomplete incurving ring allows keeping the capsular bag open and tense to allow a greater displacement of the optic, and the incurving tabs (5) provide a greater accommodation power by curving the optic and increasing its thickness.

20 Claims, 10 Drawing Sheets

ACCOMMODATIVE INTRAOCULAR LENS

The present invention relates to a new model of accommodative intraocular lens that allows changing its focus by moving the optic and by changing its thickness by incurving.

The field of application of the present invention is that of intraocular implants, and more specifically the field of lenses implanted inside the capsular bag after removing the crystalline lens.

BACKGROUND

Replacing crystalline lenses with implants has become a common operation in the field of eye surgery.

One of the problems that arise after such surgery is the impossibility of focussing both near and far when a monofocal intraocular lens is used, as the lens is fixed within the capsular bag and only one focal point can be chosen, so that the use of external lenses is necessary.

Instead, multifocal intraocular lenses provide two or more focal points, thereby avoiding the need for external lenses as they allow correcting vision at all distances.

However, multifocal intraocular lenses present drawbacks such as lack of clarity and perception of halos around light sources, among others.

These drawbacks have encouraged studying the implantation of accommodative lenses, which are lenses with a single focal point that operate as multifocal intraocular lenses since they are designed with an articulation similar to the mechanics of the crystalline lens, such that the action of the eye muscles allows changing the single focal point in order to focus objects at different distances.

Regarding the accommodation mechanisms, it has been found that the eye undergoes certain changes such as pupil contraction, contraction of the ciliary muscle, relaxation of the zonular ligament and changes in the size of the lens, such as increased thickness and curvature of its anterior face.

There exist several theories for explaining the physiological mechanism of accommodation, among which are those of Helmholtz, Tscherning, Gullstrand and Pflugk, wherein one of the most relevant factors is the action of the ciliary muscle on the eye, the crystalline lens and the incurving of its anterior face.

It is important to point out that the capsular bag is very elastic, as when it breaks it retracts such that the tear increases in size, and the folds that appear when the capsular bag is empty disappear completely when it is expanded.

After the crystalline lens has been removed the posterior capsule is left loose, as the anterior capsule is open, so that its effects on the eye are eliminated; the posterior capsule can even advance farther in an anterior direction as the anterior capsule is not retaining it.

This is observed in interventions on the crystalline lens, and occasionally the posterior capsule suffers a hernia due to capsulotomy when the posterior vitreous pressure increases.

The possibility of using a lens to replace the functions of the crystalline lens would bring us closer to a true accommodation.

A desirable optic for accommodation is one that deforms in response to a force applied on the equator of the optics.

Under the influence of this force, the optic will bulge out in an axial direction, so that the posterior and/or anterior faces will increase their curvature and therefore increase the accommodation capability of the optic. This is, the greater the capability of a lens to deform the optics the greater its accommodation capability.

Numerous implants have been designed that attempt to use the contraction and relaxation of the ciliary muscle to modify the optical capability of the eye.

In general, intraocular lenses comprise an optical part that ensures optical and particularly refractive correction and a haptic part that allows the optic to move.

Patent US2002/0138140 A1 uses a flexible annular device that deforms upon contraction of the ciliary muscle, the design of which is meant to allow the movement of the lens haptic and exert the action of the ciliary muscle to favour accommodation, which is reflected in the figures describing a posterior distension of the posterior capsule.

However, the design of the intraocular lens of patent US2002/0138140 A1 does not allow using the capsular distension at any time as a mechanism for amplifying the motion, nor does it modify the curvature or thickness of the optic.

U.S. Pat. No. 666,003B1 describes a system of levers wherein some branches pivot about others, increasing accommodation by converting the radial movement of the capsular bag into a movement of axial amplification of the optic, where the haptics or ring are designed such that they are flexible, to allow the ciliary muscle to transmit the contraction; however, its design does not allow moving the haptics, so that it cannot achieve maximum distension of the capsular bag.

Therefore, a need exists for an intraocular lens comprising means that allow both moving the optic and a greater deformation of the anterior and/or posterior deformation of the optic, thereby resulting in a greater accommodation capability.

DESCRIPTION OF THE INVENTION

The object of the present invention is therefore a new accommodative intraocular lens that amplifies the accommodation power of the optic.

In this description the terms "anterior" and "posterior" must be understood as they are used in ophthalmology. This is, "anterior" means that it is nearer the cornea and "posterior" that it is farther from the cornea. These adjectives have even been used for devices comprising the lens.

The present invention provides an accommodative intraocular lens to be placed in the capsular bag after removing the crystalline lens, that increases the accommodation capability, comprising at least one optic part, one haptic part, an incurving tab, an incomplete incurving ring and means for displacement of the haptic part.

The optic part (1) is made of a deformable, flexible material with an index of refraction similar to any intraocular lens, and comprises on the peripheral edge (2) of the optic at least one notch (3) disposed parallel to the axis that passes through the centre of the lens. This notch can be linear of polyhedral in shape.

When the peripheral edge of the optics comprises more than one notch, the notches can be disposed symmetrically or equidistant to each other and parallel to the axis that passes through the centre of the lens.

The maximum number of notches is determined by the number allowed by the perimeter of the optic.

On the peripheral edge of the optic (2), which has a trapezoidal polyhedral or saucer shape (4), is inserted at least one incurving tab (5) with an anterior or posterior angulation between 0 and 90°, while the other end of the incurving tab is inserted in the incomplete incurving ring (6).

The end of the incurving tab inserted in the incomplete incurving ring ends at a stop of the incurving tab, which can be cylindrical (7) to allow it to slide in a posterior direction and towards the optic, while the base of the incurving tabs is preferably made of a stiffer material than the optic, thereby achieving a greater deformation of the anteroposterior axis.

The incomplete incurving ring (6) comprises at least one angled branch of the ring (17), the number of angled branches of the ring being equal to the number of incurving tabs and the angled branches of the ring comprising some rails of the angled branch of the ring (18).

The haptic part (8) comprises at least one central branch (9), one lateral branch (10) and one angled branch of the haptic (11), wherein the angled branch of the haptic (11), which are not necessarily of the same size and have a polyhedral and/or semicircular shape with a rounded surface that adapts to the shape of the bag, forming an angle open towards the optic between 30 and 170 degrees, greater in large bags and smaller in small bags, but always remaining open and distending the two capsules as much as possible, as well as allowing the ring to pass on their edges.

The central branch (9) of the haptic is disposed at an angle between 5 and 90° with respect to the lateral branches.

Optionally, the angled branch of the haptic can comprise at least one adjoining lateral branch (16).

The branches do not necessarily have the same size.

In addition, the haptics comprise at least one rail of the haptic (12), one stop of the haptic (13), one spring (14) and one wedge (15).

The shape of the spring (14) can vary, preferably being semicircular and more preferably helical as it increases the amplification, and when its diameter is smaller there is a greater amplification of the anterior displacement.

The rail of the haptic (12) constitutes the sliding means for the parts of the haptic.

The wedge (15), which is designed to be the supporting point of the lateral branches of the haptic, has a polyhedral shape and one of its faces is adapted to the surface of the lateral branch of the haptic with a straight or curved shape and in an angle between 0 and 90°, the number of wedges being equal to the number of lateral branches.

Alternatively, as a means for transmitting the motion and/or stopping the moving parts and/or amplification, a toothed wheel (22) and some teeth (23) are provided.

This structure provides several advantages.

In addition to the displacements of the optic caused by the necessary means, such as the haptics, the accommodation is increased by the incurving and/or changes in thickness of the optic and/or the distension of the posterior capsule.

Considering that the most important changes that occur when the crystalline lens is removed surgically is that the central part of the anterior capsule is eliminated and the tension of the capsules is lost as the bag is now empty, a new model of lens is proposed that achieves the postero-anterior displacement of the lens, a modification of the curvature of the optic and changes in the thickness of the optic aided by the maximum distension of the posterior capsule, which is as elastic as possible and thus can favour this movement.

The lens is displaced using the contraction of the ciliary muscle and more importantly by the forward displacement of the posterior capsule produced by the vitreous pressure, achieving a greater accommodative capability by adding to the displacement an incurving and changes in the thickness of the optic.

For this purpose, the accommodative lens of the present invention is provided with haptics and an incomplete incurving ring that is sufficiently stiff to maintain the capsular bag open and is tensioned such that the elastic capability of the bag remains largely intact.

The advantage of maintaining the bag completely distended and open is that it makes it more sensitive to the postero-anterior displacement of the posterior capsule when the ciliary muscle contracts and the pressure of the vitreous cavity and its content increase, facilitating both the movement of the lens and its return to its resting position without hindrance.

The stiffness of the incomplete incurving ring allows the lens to stay stable when not accommodating and causes changes in the curvature and thickness of the optic when accommodating, as it retains the incurving tabs (5) and allows its displacement towards the centre when the optic rises.

Another advantage of the accommodative intraocular lens of the present invention are the notches on the edge of the optic, which modify both the curvature and the thickness of the lens and therefore increase the accommodative capability of the lens.

In this sense, it must be remarked that the greater the number of notches and/or their size, the greater the thickness of the optic and therefore the greater the accommodation.

In addition, the polyhedral, trapezoidal or saucer-shaped edge of the optic perimeter increases the thickness of the lens when the incurving takes place upon its anterior displacement, resulting in an increased accommodative capability of the lens.

Accommodation is also increased by combining several optics in the same lens.

In addition, due to the configuration of the angled branches of the ring (17), their displacement favours the movement of the optic in an anterior sense with accommodation and in a posterior sense in the accommodative resting position.

Thus, according to a preferred embodiment of the invention the configuration of the accommodative intraocular lens allows amplifying the accommodation power by more than 500%.

The materials used to make the different components of the accommodative intraocular lens are biocompatible materials for intraocular use, such as acrylates and methacrylates (such as polymethylmethacrylate), silicone, elastomers, etc. These materials can deform elastically, allowing to fold the lens to insert it in the capsular bag through a small incision and at the same time are sufficiently stiff to allow keeping the capsular bag completely open and tensioned.

DETAILED DESCRIPTION OF THE INVENTION

Different embodiments of the invention are described below which are not the only ones possible, so that the scope of protection of the present invention should extend to any possible embodiments that adopt the essential technical elements that characterise this invention.

The first embodiment of the intraocular lens is described with reference to FIGS. 1 to 10.

Figure 1:
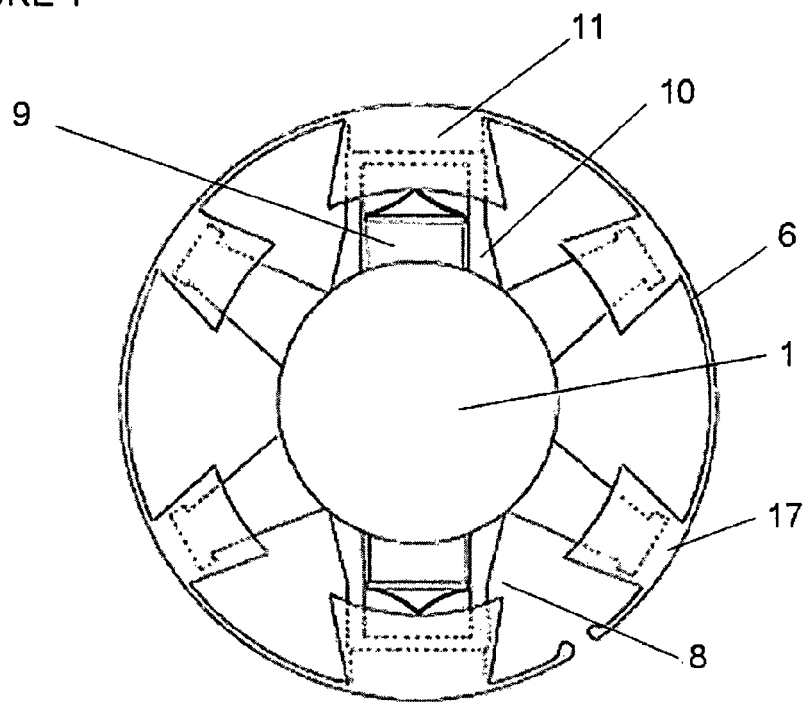
FIG. 1 is a view of the anterior face of an accommodative intraocular lens of a first embodiment of the invention showing the optic (1), the incurving tab (5), the incomplete incurving ring (6), the stop of the cylindrical incurving tab (7), the haptic part (8), the central branch (9), the lateral branch (10), the angled branch of the haptic (11) and the angled branch of the ring (17).

The intraocular lens shown in FIG. 1 comprises an optical part (1) that in turn comprises a lens, a haptic part (8), incurving tabs (5) and an incomplete incurving ring (6) which in turn comprises angled branches of the ring (17), wherein the materials of which the various components of the intraocular lens are made are biocompatible materials.

Figure 2:
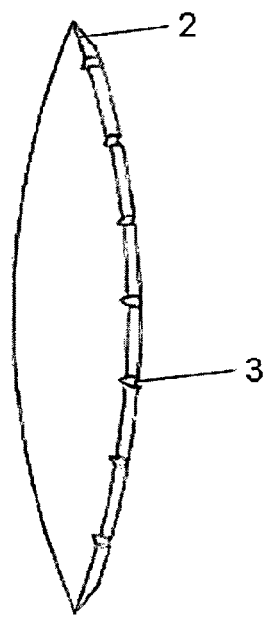
FIG. 2 is a cross-sectional view of the optic (1) showing the peripheral edge (2) of the optic and the notches (3).
Figure 3:
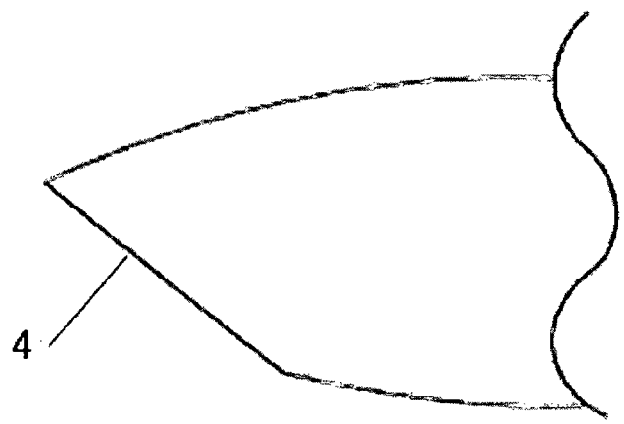
FIG. 3 is a cross-sectional view of the optic (1) showing the saucer-shaped peripheral edge (4) of the optic.

The optic part (1) constitutes the central part of the intraocular lens and comprises a lens with some notches, such as those shown in FIG. 2, preferably with a triangular shape, disposed parallel to the axis that passes through the centre, symmetrically and/or equidistant from each other, which provide the anteroposterior incurving of the lens (1) and a peripheral edge of the lens (2) such as that shown in FIG. 2 and FIG. 3 with a trapezoidal or saucer shape on the ends of the optic that enhances the increase in thickness of the lens (1) when the incurving occurs.

The haptic part (8) is the mobile device of the lens and when inserted in the capsular bag rests on its outermost edge and on both capsules.

The haptic part comprises a second part (20) that is mobile and a first part (21) on which the slides the second part (20), shown in FIGS. 6 to 10.

Figure 6:
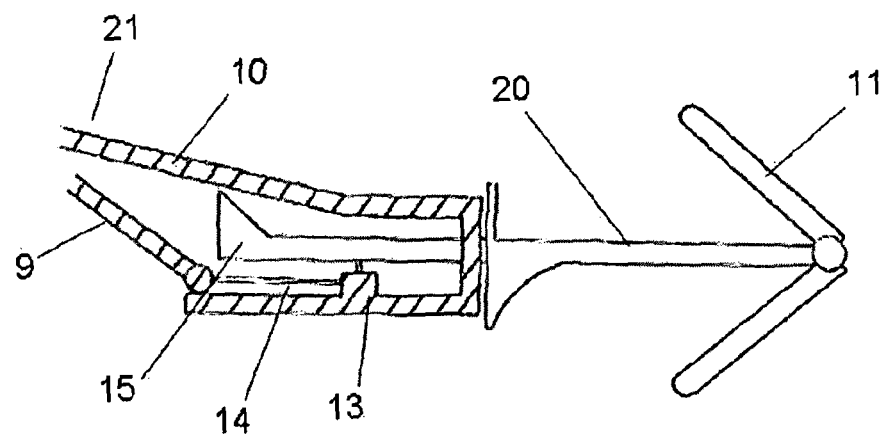
FIG. 6 is a cross-sectional view of the first part (21) of the haptic (8) and the second part (20) of the haptic (8) showing the central branch (9), the lateral branch (10), the angled branch of the haptic (11), the spring (14), the wedge (15) and the stop of the haptic (13).
Figure 7:
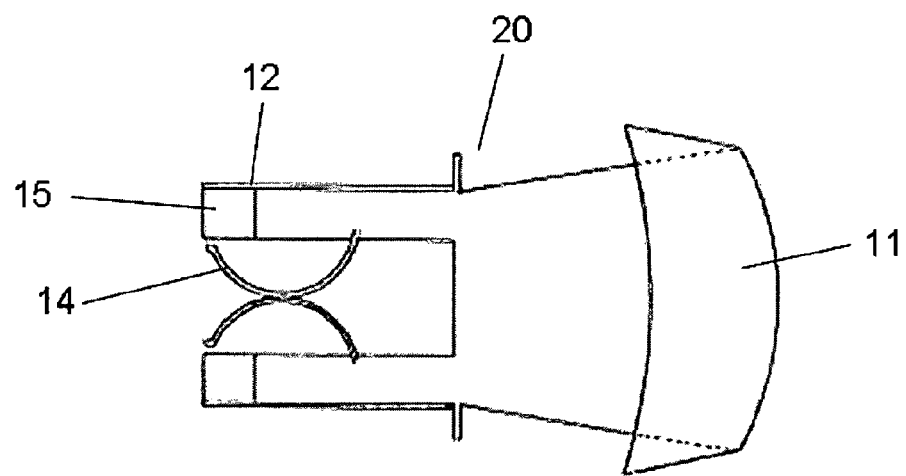
FIG. 7 is a front view of the second part (20) of the haptic (8) showing the rails of the haptic (12), the spring (14), the wedge (15) and the angled branch of the haptic (11).

The second part (20) of the haptic (8) shown in FIGS. 6 and 7 comprises at least a spring (14), an angled branch of the haptic (11), a wedge (15) and rails of the haptic (12).

Figure 8:
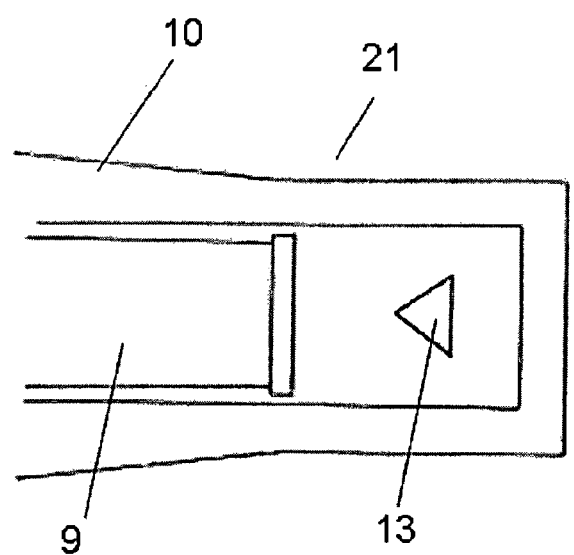
FIG. 8 is a front view of the first part (21) of the haptic (8) on which slides the second part of the haptic (20) showing the central branch (9), the lateral branch (10) and the stop of the haptic (13).
Figure 9:
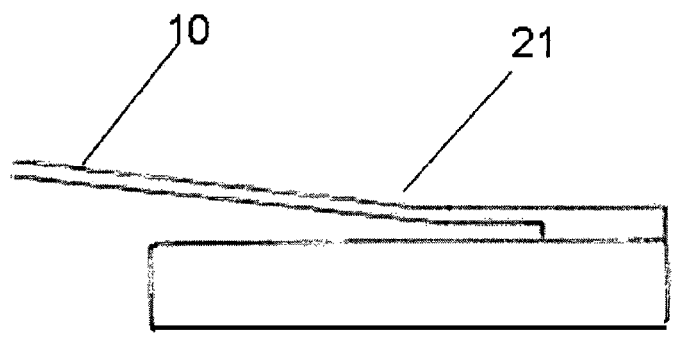
FIG. 9 is a side view of the first part (21) of the haptic (8).
Figure 10:
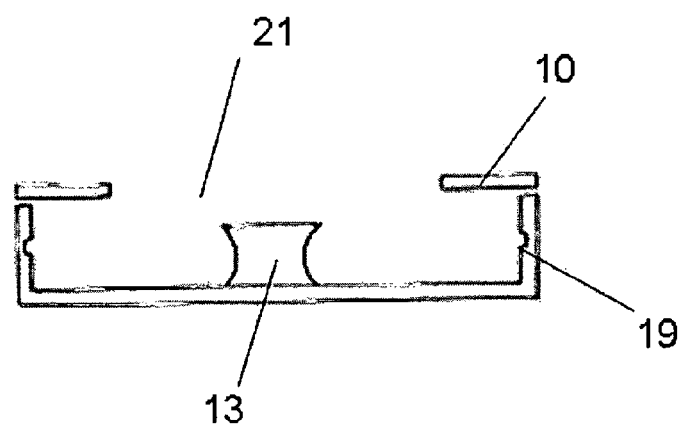
FIG. 10 is a cross-sectional view of the first part (21) of the haptic (8).
Figure 11:
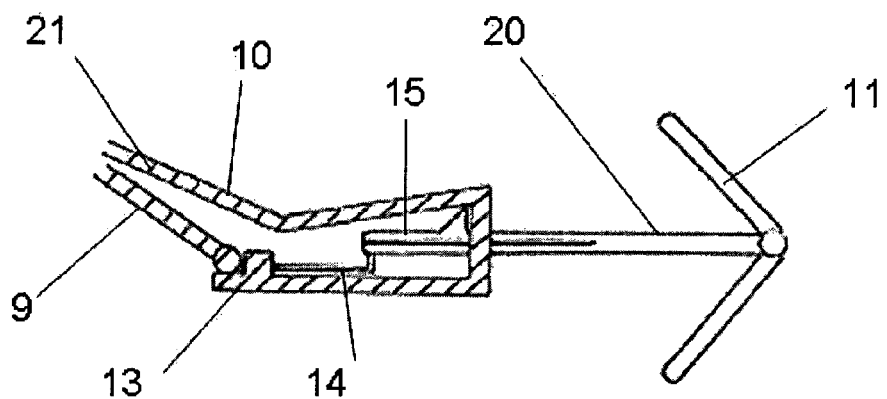
FIG. 11 is a cross-sectional view of the first part (21) of the haptic (8) and the second part (20) of the haptic (8) showing the central branch (9), the lateral branch (10), the angled branch of the haptic (11), the spring (14), the wedge (15) and the stop of the haptic (13) of a second embodiment of the invention.
Figure 12:
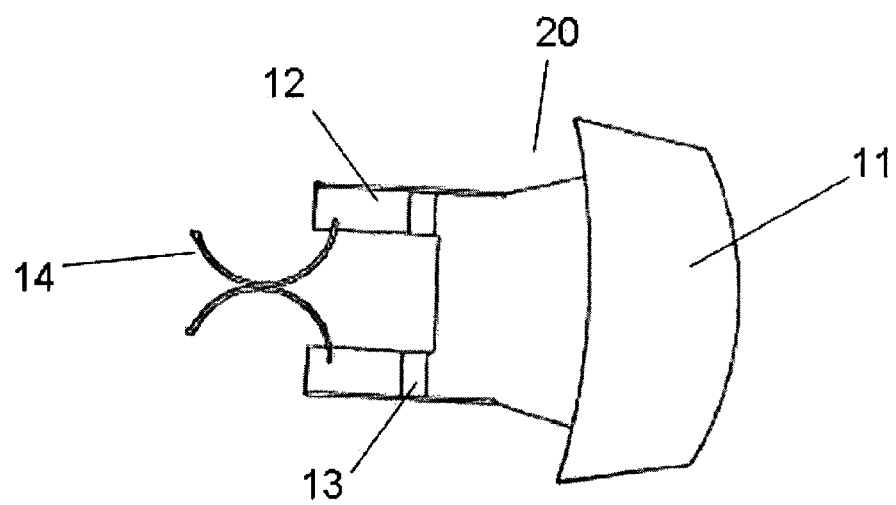
FIG. 12 is a front view of the second part (20) of the haptic (8) showing the rails of the haptic (12), the spring (14), the wedge (15) and the angled branch of the haptic (11) of a second embodiment of the invention.
Figure 13:
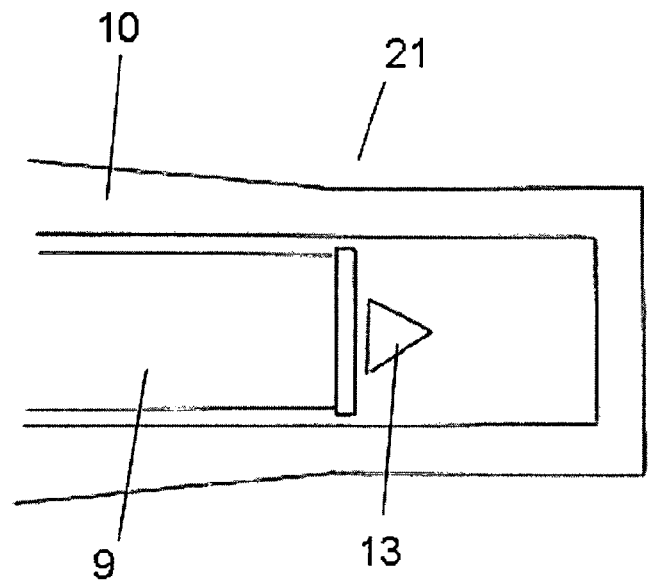
FIG. 13 is a front view of the first part (21) of the haptic (8) on which slides the second part of the haptic (20) showing the central branch (9), the lateral branch (10) and the stop of the haptic (13) of a second embodiment of the invention.
Figure 14:
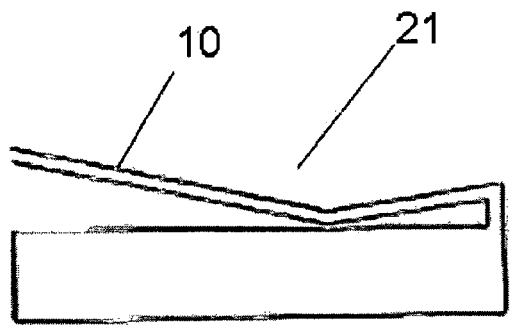
FIG. 14 is a side view of the first part (21) of the haptic (8) of a second embodiment of the invention.

The second part (20) of the haptic (8) shown in FIGS. 6 and 7 has a wide base that rests on and adheres to the zonule, sliding inside the first part (21) shown in FIGS. 8, 9 and 10 by means of some rails of the haptic (12) and grooves (19) and is retained by a spring device (14) that is connected to the central branch (9) to prevent its displacement towards the inside of the bag. The grooves (19) can be straight or have an open angle ranging from 0 to 80 degrees towards the optic.

When the second part (20) moves, the wedge (15) will slide, moving and lifting the lateral branches (10) joining them to the first part (21), and moving the spring (21) that is connected to the central branch (9), thereby lifting the optic part, which begins to move aided by the pressure of the vitreous humour and the action of the lateral branches (10) and central branches (9) that are disposed at an angle between 5 and 90 degrees, amplifying the displacement by more than 400%.

The spring (14) allows returning to the resting position and has a semicircular shape, as shown in FIG. 7, allowing a greater amplification of the anterior displacement by its smaller diameter. The spring is preferably helical in shape as this increases the amplification.

The stop of the haptic (13) shown in FIGS. 6, 8 and 10 with a polyhedral shape and which limits the movement in one direction allows deforming the spring (14), which due to its design and the contact with the faces of the stop can deform in a horizontal sense and in an anterior vertical sense, allowing to move the optic even farther forward.

The polyhedral wedge (15) shown in FIGS. 6 and 7 is the supporting point of the lateral branches of the haptic, one of its faces being adapted to the surface of the lateral branch of the haptic with a straight or curved shape and an angled between 0 and 90 degrees, the number of wedges (15) being equal to the number of lateral branches (10).

The incomplete incurving ring (6) is designed to be inserted through a small incision and is sufficiently stiff to jeep the capsule stable and act as a stop for the incurving tabs (5) of the edge of the optic (1) to change the thickness of the lens (1).

Figure 4:
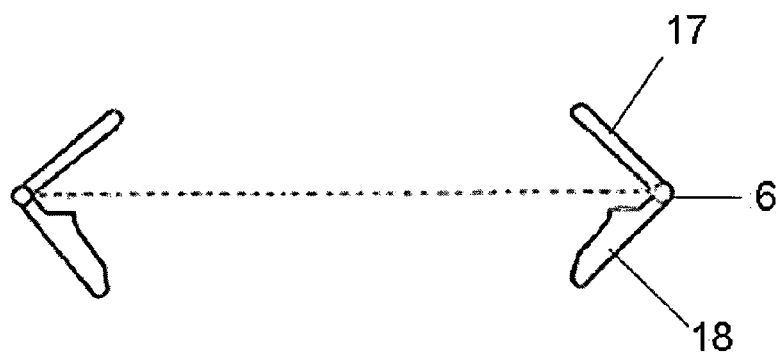
FIG. 4 is a cross-sectional view of the incomplete incurving ring (6) showing the angled branches of the ring (17) and the rail of the angled branch of the ring (18).

FIG. 4 shows a cross-sectional view of the incomplete incurving ring (6) showing the angled branches of the ring

Figure 5:
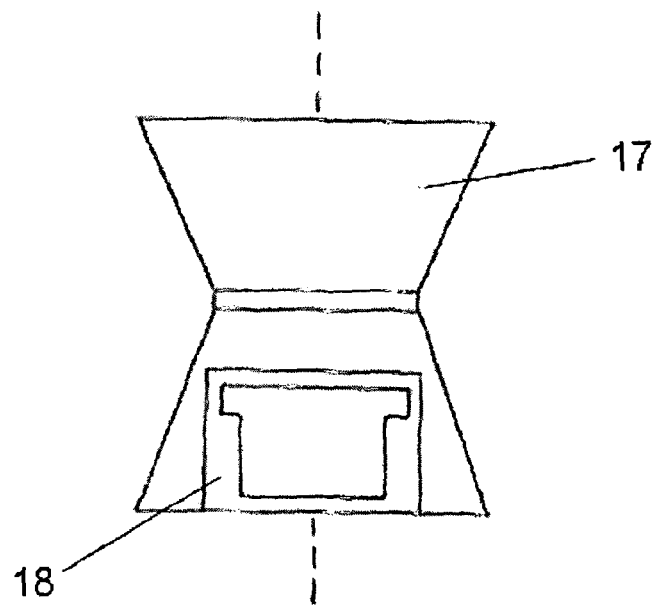
FIG. 5 is a view of the inner face of the angled branches of the ring (17).

(17) and the rail of the angled branch of the ring (18). FIG. 5 shows the inner face of the angled branches of the ring (17).

In this first embodiment the haptic is displaced toward the zonule by the displacement of the distended posterior capsule and the vitreous pressure.

The second embodiment is a variant of the first embodiment and comprises FIGS. 1 to 5. The characteristics that modify the first embodiment are shown in FIGS. 10 to 14.

This second embodiment makes use of the contraction of the ciliary muscle in addition to the displacement of the posterior capsule to slide the haptic towards the optic, which is why the grooves (19) have an angled closed towards the optic.

The intraocular lens of the third embodiment comprises most of the characteristics of the first embodiment. Thus, the same elements or the elements that carry out the same function are designated by the same numerals.

Figure 16:
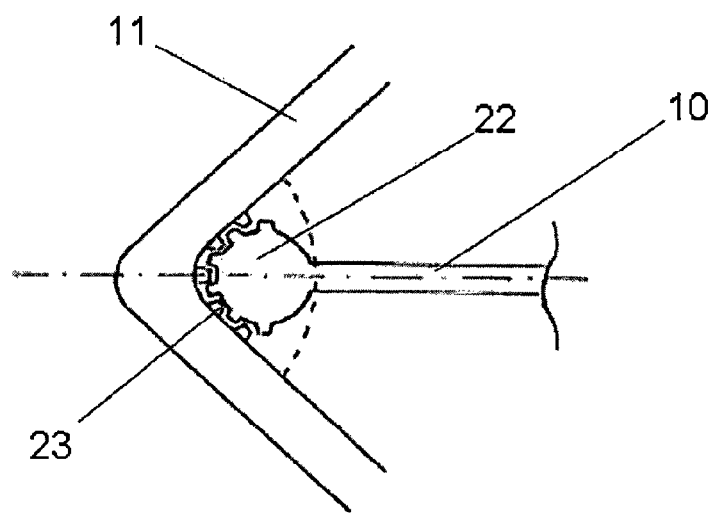
FIG. 16 is a cross-sectional view of the haptic part (8) of a third embodiment of the invention showing the lateral branch (10), the angled branch of the haptic (11), the toothed wheel (22) and the teeth (23).

The characteristics that modify the first embodiment are shown in FIG. 16.

The displacement of the capsule and the vitreous pressure force a postero-anterior rotation of the angled branches of the haptic (11), amplifying the movement of the lateral branches (10) by means of the toothed wheel (22) and the teeth (23) shown in FIG. 16 and moving it in an anterior direction within the bag.

The central branch (9) is disposed at an angle between 5 and 90 degrees with respect to the lateral branches (10), enhancing the lifting and/or incurving effect by swivelling the angled branches of the haptic (11) and further enhancing this effect by increasing the number of lateral and/or angled branches of the haptic and/or central branches. In addition, the lateral branches can be located centrally and the central branch can be located laterally.

The incomplete incurving ring (6) adds stability to the lens in the resting position, keeps the bag open by the angled branches of the ring (17) and allows the incurving of the optic by sliding the incurving tabs (5) in a posterior sense.

Figure 17:
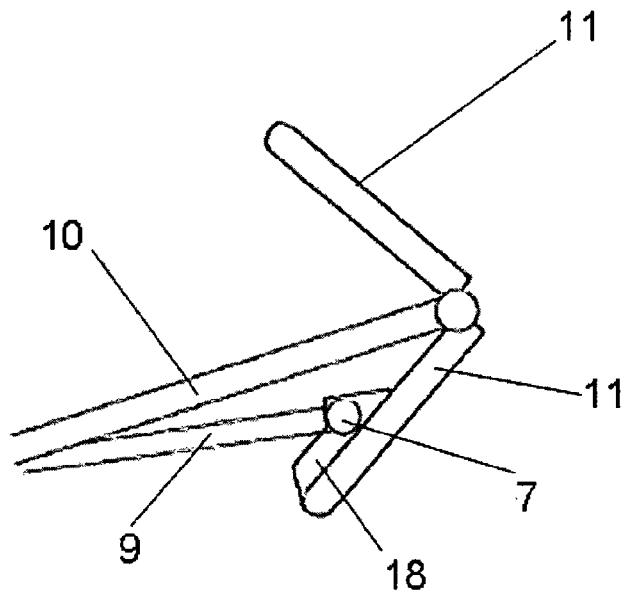
FIG. 17 is a cross-sectional view of the haptic part (8) of a third embodiment of the invention showing the angled branch of the haptic (11), the lateral branch (10), the central branch (9), the rail of the angled branch of the ring (18) and the stop of the cylindrical incurving tab (7).
Figure 18:
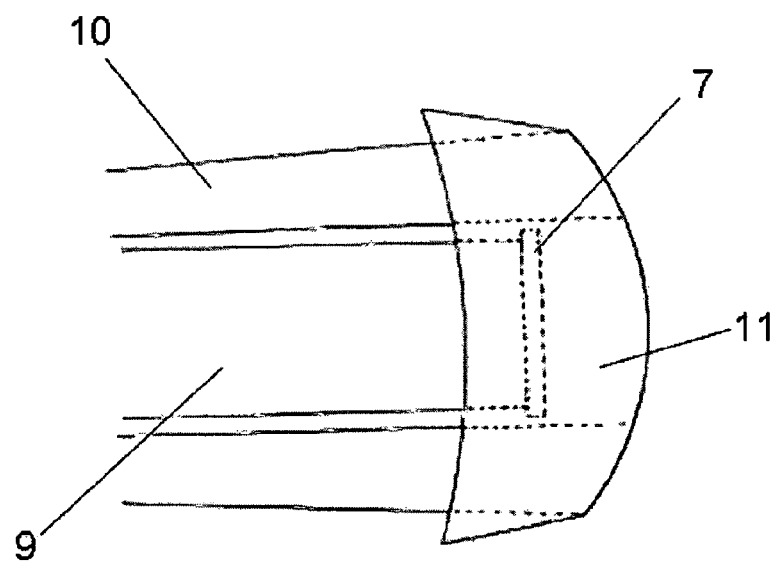
FIG. 18 is a front view of the haptic part (8) of a third embodiment of the invention showing the angled branch of the haptic (11), the lateral branch (10), the central branch (9) and the stop of the cylindrical incurving tab (7).
Figure 19:
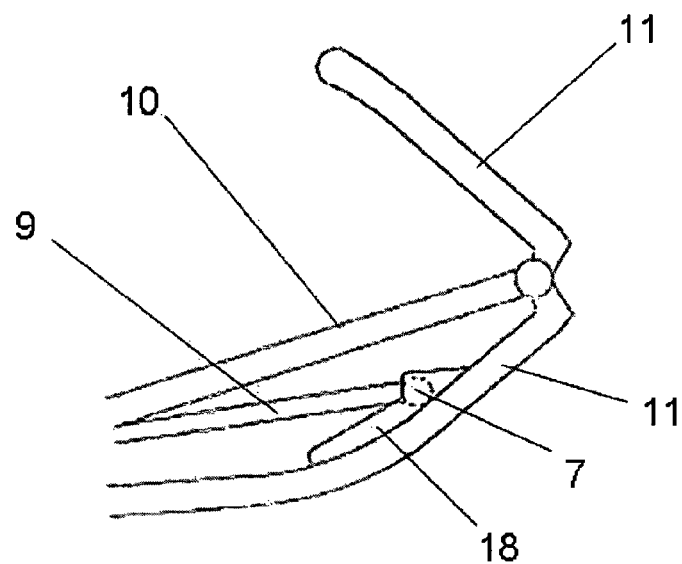
FIG. 19 is a cross-sectional view of the haptic part (8) of a third embodiment of the invention showing the angled branch of the haptic (11), the lateral branch (10), the central branch (9), the rail of the angled branch of the ring (18) and the stop of the cylindrical incurving tab (7).
Figure 20:
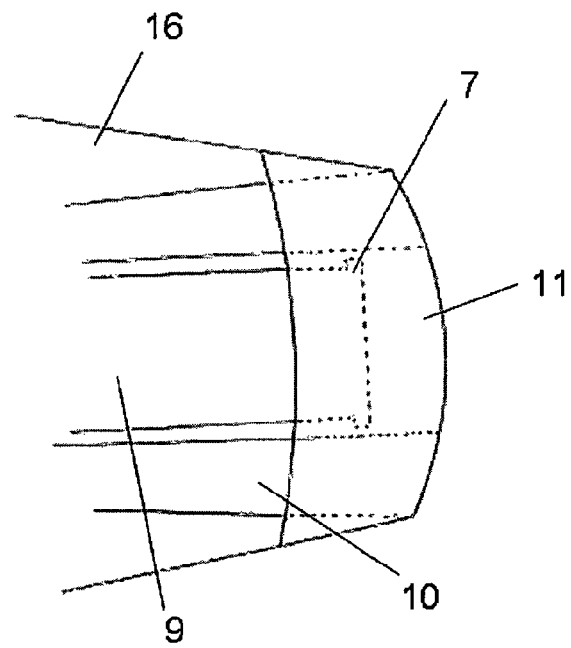
FIG. 20 is a front view of the haptic part (8) of a third embodiment of the invention showing the angled branch of the haptic (11), the lateral branch (10), the central branch (9), the stop of the cylindrical incurving tab (7) and the adjoining lateral branch (16).

When the optic part (1) moves in an anterior sense, the incurving tabs (5) move in a posterior and inward direction along the rails of the angled branch of the ring (18) located on the angled branches of the ring (17), causing it to curve in and achieving a greater anterior displacement of the optic part (1) as well as allowing to increase its anteroposterior thickness by virtue of its trapezoidal edge (4) and the incurving notches (3). In addition, the design of the incomplete incurving ring (6) keeps the bag open and the angled branch of the haptic (11) can be short as shown in FIG. 17 or 18, or long as shown in FIG. 19.

Figure 15:
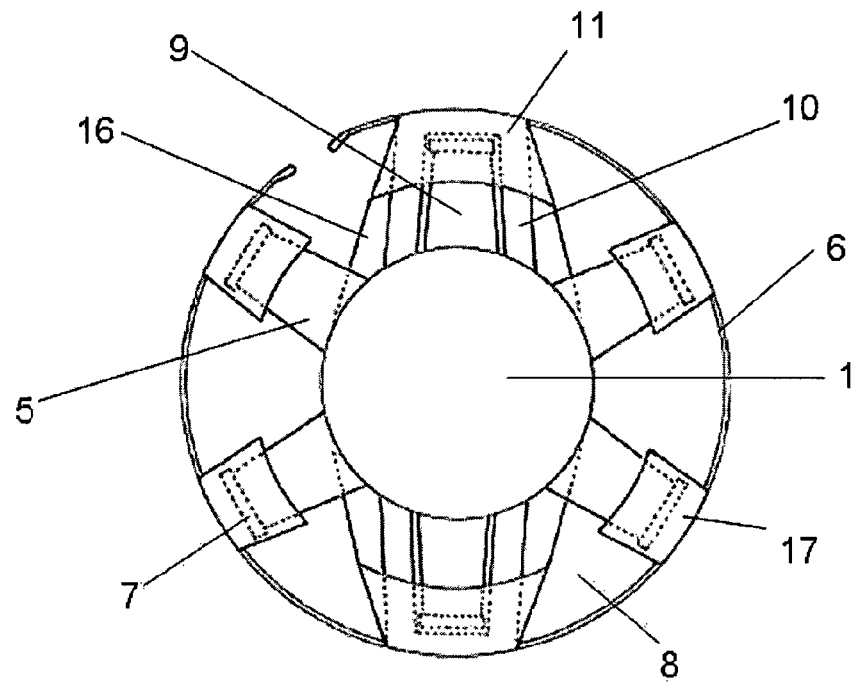
FIG. 15 is a view of the anterior face of an accommodative intraocular lens of a third embodiment of the invention showing the optic (1), the incurving tab (5), the incomplete incurving ring (6), the stop of the cylindrical incurving tab (7), the haptic part (8), the central branch (9), the lateral branch (10), the angled branch of the haptic (11), the angled branch of the ring (17) and the adjoining lateral branch (16).

Optionally, in all the embodiments described above the haptic part can comprise at least one adjoining lateral branch (16). A corresponding variant of the previous embodiments is shown in FIGS. 15 y 20.

The invention claimed is:

1. Accommodative intraocular lens for implantation in the capsular bag of an eye, characterised in that it comprises at least one optic part (1) which in turn comprises at least one incurving notch (3) and a peripheral edge of the optic (2) having a trapezoidal polyhedral shape; a haptic part (8) that in turn comprises at least one central branch (9), one lateral branch (10) and one angular branch of the haptic (11) of a material stiffer than a material of the optic; an incomplete incurving ring (6) that in turn comprises at least one angled branch of the ring (17); one incurving tab (5) and means for sliding and/or stopping and/or amplifying the moving parts.

2. Intraocular lens according to claim 1, characterised in that the notches (3) and/or the peripheral edge of the optic (2) have a polyhedral shape.

3. Intraocular lens according to claim 1, characterised in that the notches (3) and/or the peripheral edge of the optic (2) have a linear shape.

4. Intraocular lens according to claim 1, characterised in that the notches (3) and/or the edge of the optic (2) present a combination of linear and polyhedral shapes.

5. Intraocular lens according to claim 1, characterised in that the notches (3) of the peripheral edge of the optic (2) are located symmetrically and/or equidistant from one another.

6. Intraocular lens according to claim 1, characterised in that the peripheral edge of the optic (2) has a trapezoidal or saucer shape.

7. Intraocular lens according to claim 1, characterised in that the angled branch of the ring (17) comprises means (27) for sliding the incurving tab (5) and keeps open the capsular bag.

8. Intraocular lens according to claim 1, characterised in that the haptic part (8) comprises at least one central branch (9), one lateral branch (10), one angled branch of the haptic (11) and/or one adjoining lateral branch (16).

9. Intraocular lens according to claim 1, characterized in that the angled branches of the haptic (11) have a polyhedral shape with a rounded surface adapted to the shape of the bag.

10. Intraocular lens according to claim 1, characterised in that the angled branches of the haptic (11) have an arc shape with a rounded surface adapted to the shape of the bag.

11. Intraocular lens according to claim 1, characterised in that all the angled branches of the haptic (11) are the same size.

12. Intraocular lens according to claim 1, characterised in that all the angled branches of the haptic (11) are not the same size.

13. Intraocular lens according to claim 1, characterised in that the angle of the angled branches of the haptic (11) lies between 30 and 170° and the angle of the angled branches of the haptic faces towards the optic.

14. Intraocular lens according to claim 1, characterised in that the incurving tabs (5) have an anterior or posterior angulation between 0° and 90°.

15. Intraocular lens according to claim 1, characterised in that the central branch of the haptic (9) is disposed at an angled between 5° and 90° with respect to the lateral branch (10).

16. Intraocular lens according to claim 1, characterised in that the haptic part comprises a first part and a second part, wherein the first part comprises a stop of the haptic (13) and a groove (19) and wherein the second part comprises at least one wedge (15), one spring (14) and one rail of the haptic (12).

17. Intraocular lens according to claim 1, characterised in that the haptic part comprises a first part and a second part, wherein the second part comprises a number of wedges (15) equal to the number of lateral branches (10) and the wedges have a polyhedral shape.

18. Intraocular lens according to claim 1 characterised in that the haptic part comprises a first part and a second part, wherein the second part comprises a wedge (15) having at least one face of the wedge adapted to the surface of the lateral branch of the haptic (10) at an angle between 0° and 90°.

19. Intraocular lens according to claim 1 characterised in that the haptic part comprises a first part and a second part, wherein the second part comprises a spring (14) that has a semicircular shape, preferably helical.

20. An accommodative intraocular lens for implantation in the capsular bag of an eye, comprising:
- at least one optic part (1);
- a haptic part (8) having a first part and a second part in sliding engagement with the first part, the first part of the haptic coupled to the optic and comprising at least one central branch (9) and one lateral branch (10), the second part of the haptic comprising an angular branch of the haptic (11);
- an incomplete incurving ring (6) comprising at least one angled branch of the ring (17); and
- at least one incurving tab (5) coupled at a first end of the tab to the optic and coupled at a second end of the tab to an angled branch of the ring.

* * * * *